United States Patent
Vittur et al.

(10) Patent No.: US 10,577,534 B2
(45) Date of Patent: Mar. 3, 2020

(54) WELL TREATMENT MATERIAL FOR SLOW RELEASE OF BIOCIDE

(71) Applicant: Baker Hughes, a GE company, LLC, Houston, TX (US)

(72) Inventors: Brandon Vittur, Houston, TX (US); Gordon Mackenzie, Cypress, TX (US); Sahar Mouallem, Conroe, TX (US)

(73) Assignee: BAKER HUGHES, A GE COMPANY, LLC, Houston, TX (US)

( * ) Notice: Subject to any disclaimer, the term of this patent is extended or adjusted under 35 U.S.C. 154(b) by 109 days.

(21) Appl. No.: 15/481,614

(22) Filed: Apr. 7, 2017

(65) Prior Publication Data
US 2017/0292060 A1  Oct. 12, 2017

Related U.S. Application Data

(60) Provisional application No. 62/320,181, filed on Apr. 8, 2016.

(51) Int. Cl.
| | |
|---|---|
| *C09K 8/62* | (2006.01) |
| *C02F 1/76* | (2006.01) |
| *C09K 8/60* | (2006.01) |
| *C09K 8/035* | (2006.01) |
| *A01N 25/08* | (2006.01) |
| *A01N 59/00* | (2006.01) |
| *B01J 20/10* | (2006.01) |
| *C01B 11/02* | (2006.01) |
| *C02F 1/50* | (2006.01) |
| *C09K 8/80* | (2006.01) |
| *B01J 20/20* | (2006.01) |
| *B01J 20/28* | (2006.01) |
| *E21B 37/06* | (2006.01) |
| *E21B 43/26* | (2006.01) |
| *E21B 43/267* | (2006.01) |
| *C02F 1/42* | (2006.01) |
| *C02F 103/10* | (2006.01) |

(52) U.S. Cl.
CPC ............ *C09K 8/62* (2013.01); *A01N 25/08* (2013.01); *A01N 59/00* (2013.01); *B01J 20/103* (2013.01); *B01J 20/20* (2013.01); *B01J 20/2805* (2013.01); *B01J 20/28047* (2013.01); *C01B 11/022* (2013.01); *C02F 1/50* (2013.01); *C02F 1/76* (2013.01); *C09K 8/035* (2013.01); *C09K 8/605* (2013.01); *C09K 8/80* (2013.01); *E21B 37/06* (2013.01); *E21B 43/26* (2013.01); *E21B 43/267* (2013.01); *C02F 1/42* (2013.01); *C02F 2103/10* (2013.01); *C02F 2303/04* (2013.01); *C02F 2305/02* (2013.01); *C02F 2305/14* (2013.01)

(58) Field of Classification Search
None
See application file for complete search history.

(56) References Cited

U.S. PATENT DOCUMENTS

| | | | |
|---|---|---|---|
| 3,063,218 A | 11/1962 | Pernert et al. | |
| 9,029,300 B2 | 5/2015 | Gupta | |
| 2009/0312428 A1* | 12/2009 | Figueredo | A01N 33/12 514/588 |
| 2012/0073821 A1* | 3/2012 | Holtsclaw | C09K 8/035 166/310 |

OTHER PUBLICATIONS

Baker Hughes Incorporated; Sorb Family of Solid Chemicals: Offer long-lasting flow assurance; 1 page; 2014; U.S.
Baker Hughes Incorporated; Sorb Ultra Solid Inhibitors: Providing multi-year flow assurance and mitigate intervention costs for offshore wells; 2 pages; 2014; U.S.
Baker Hughes Incorporated; H2prO HD: Safe and Effective Chlorine Dioxide Treatment; 33 pages; 2015; U.S.

* cited by examiner

*Primary Examiner* — John J Figueroa
(74) *Attorney, Agent, or Firm* — Greenberg Traurig LLP

(57) ABSTRACT

A well treatment material for introduction into a subterranean formation is provided. The well treatment material can include a biocide collected onto a sorbent. The biocide can be capable of being desorbed at a generally constant rate over an extended period of time into the subterranean formation. The biocide can be an oxidizing biocide or a non-oxidizing biocide. The sorbent material can include one or more of an absorbent material and an adsorbent material. The biocide can be chlorine dioxide. The sorbent can be one or more of silica gel and graphite.

15 Claims, No Drawings

WELL TREATMENT MATERIAL FOR SLOW RELEASE OF BIOCIDE

RELATED APPLICATIONS

This application claims the benefit, and priority benefit, of U.S. Provisional Patent Application Ser. No. 62/320,181, filed Apr. 8, 2016, the disclosure and contents of which are incorporated by reference herein in their entirety.

BACKGROUND

Description of the Related Art

Oil and/or gas production wells often contain hydrogen sulfide ($H_2S$), iron sulfide scale (FeS), bacteria and bacterial deposits. Accumulation of these materials can reduce well productivity. Well treatment materials can be used to prevent or reduce formation of these materials. It is often desired to introduce these well treatment materials into the wells over an extended period of time (i.e., "slow-release") such that continuous attention to the well by operators over prolonged periods is unnecessary. Improvements in this field of technology are desired.

SUMMARY

Disclosed herein are various illustrative embodiments of a well treatment material for introduction into a subterranean formation. In certain aspects, the well treatment material can include a biocide collected onto a sorbent. The biocide can be capable of being desorbed at a generally constant rate over an extended period of time into the subterranean formation. The biocide can be an oxidizing biocide or a non-oxidizing biocide. The sorbent material can include one or more of an absorbent material and an adsorbent material. The biocide can be chlorine dioxide. The sorbent can be one or more of silica gel and graphite.

Also disclosed herein are various illustrative embodiments of an oxidizing material for use in a producing well. In certain aspects, the oxidizing material can include a biocide collected onto a sorbent material. The sorbent material can include one or more of an absorbent material and an adsorbent material. The sorbent material can include one or more of silica gel and graphite. The sorbent material can be disposed in a proppant pack. The biocide can be chlorine dioxide.

Also disclosed herein are various illustrative embodiments of an oxidizing material for use in a hydraulic fracturing operation. In certain aspects, the oxidizing material can include a biocide collected onto a sorbent material. The sorbent material can include one or more of an absorbent material and an adsorbent material. The sorbent material can include one or more of silica gel and graphite. The sorbent material can be disposed in a proppant pack. The biocide can be chlorine dioxide.

Also disclosed herein are various illustrative embodiments of a fracturing fluid. In certain aspects, the fracturing fluid can include a carrier fluid, a polymer that is soluble in the carrier fluid, a proppant and an oxidizing material comprising a biocide collected onto a sorbent material. The sorbent material can include one or more of an absorbent material and an adsorbent material. The sorbent material can include one or more of silica gel and graphite.

Also disclosed herein are various illustrative embodiments of a method for treating a hydrocarbon-bearing formation. In certain aspects, a fracturing fluid can be discharged into a downhole fracture in the hydrocarbon-bearing formation. The fracturing fluid can include a carrier fluid, a polymer that is soluble in the carrier fluid, a proppant and an oxidizing material comprising chlorine dioxide collected onto a sorbent material.

Also disclosed herein are various illustrative embodiments of an apparatus for treatment of an aqueous stream. In certain aspects, the apparatus can include an ion exchange resin bed, a treatment material disposed in the ion exchange resin bed, and a screen filter disposed adjacent the ion exchange resin bed and capable of filtering the aqueous stream. In certain aspects, the treatment material can be a carbon dioxide biocide collected onto a sorbent. The apparatus can be mounted on a skid or trailer for easy of portability.

DETAILED DESCRIPTION

Various illustrative embodiments of a well treatment material for use in treatment of a well in a subterranean formation are disclosed herein. In certain illustrative embodiments, the well treatment material can comprise a sorbent material and at least one well treatment agent that is collected onto the sorbent material.

In certain illustrative embodiments, the well treatment agent comprises a biocide. The biocide can be, for example, chlorine dioxide ($ClO_2$). Chlorine dioxide can be used to mitigate formation of, for example, hydrogen sulfide, bacteria, iron sulfide and unwanted polymers. Chlorine dioxide kills bacteria by altering the permeability of the outer cell membrane and attacking cell physiological functions. Sulfate-reducing bacteria and acid-producing bacteria are especially vulnerable to chlorine dioxide oxidation. Chlorine dioxide has oxidizing properties that will destroy hydrogen sulfide and iron sulfide contaminants. Other examples of biocides that may be utilized include other oxidizing and non-oxidizing biocides.

In certain illustrative embodiments, the sorbent material comprises a substrate. For example, the substrate can be one or more of silica gel or graphite. There are likely a number of other sorbent materials that can also be utilized within the scope of the presently disclosed subject matter. Factors that may be considered when selecting a particular sorbent material can include, for example, speed of slow release and capability for collection of the particular biocide that is selected, as it is anticipated that the more biocide material that is collected, the slower the release will be.

In certain illustrative embodiments, collection of biocide onto the sorbent can occur via one or more of absorption and adsorption. Absorption is the process in which a chemical is dissolved by a liquid or a solid absorbent. Thus, absorption can occur, for example, when the biocide enters the sorbent fully. Adsorption is the process in which a chemical adheres to the surface of the adsorbent. Adsorption is a surface-based process where a film of adsorbate is created on the surface while absorption involves the entire volume of the absorbing substance. Thus, adsorption can occur, for example, when the biocide sits on top of the sorbent as an outer layer.

In certain illustrative embodiments, the well treatment material can contain an amount of well treatment agent that is sufficient to produce the desired well treatment properties. For example, if the biocide is chlorine dioxide, the amount of chlorine dioxide that is present in the well treatment material can be of a concentration up to about 35 percent, which would make the material suitable for shipping with minimum explosion hazards, in certain illustrative embodiments.

In certain illustrative embodiments, the well treatment material can be slow released into a producing well. For example, the producing well can be an oil and gas well in certain illustrative embodiments.

In certain illustrative embodiments, the well treatment material can also be slow released into a well that is undergoing hydraulic fracturing. For example, the well that is undergoing hydraulic fracturing will have the solid slow release materials placed in the fractures during the stimulation program and will remain in place during the production phase to provide longer protection downhole.

The well treatment material may be used to control the rate of release of well treatment agent into the well. In certain illustrative embodiments, the well treatment agent will slowly desorb from the sorbent material as fluid from the well passes through or circulates around the well treatment material. In so doing, the well treatment material is characterized by time-release capabilities. Gradual desorption or "slow-release" of the well treatment agent insures that it is available in the well for extended periods of time, without the need for continuous attention by operators over prolonged periods.

In certain illustrative embodiments, the sorbent material can be incorporated into a permeable "proppant pack" to facilitate the slow release of the well treatment agent into the well. For example, the proppant can be a conventional particulate material employed in hydraulic fracturing operations. The proppant can be suspended in a fracturing fluid and pumped into the created fracture. The proppant pack will remain in the fracture to hold the fractures open, thus forming conductive channels through which fluids may flow to (or from) the wellbore. The biocide can be collected by the sorbent material, and the sorbent material can be added to the proppant pack to allow for the slow release of the biocide during production. This would be beneficial for wells that have, for example, naturally occurring bacteria and $H_2S$.

Thus, in certain illustrative embodiments, the fracturing fluid can comprise a carrier fluid, a polymer that is soluble in the carrier fluid, a proppant and an oxidizing material comprising a biocide collected onto a sorbent material.

In certain illustrative embodiments, a method of forming a well treatment material is provided. Biocide can be circulated through a closed container that houses a sorbent material. The sorbent material can be saturated with the biocide. After the sorbent is saturated, the container can be emptied and the well treatment material can be added to the proppant pack for use in the production well In certain illustrative embodiments, a well treatment material for introduction into a subterranean formation is provided. The well treatment material can comprise a biocide collected onto a sorbent. The biocide can desorb at a generally constant rate over an extended period of time into the subterranean formation.

In certain illustrative embodiments, the biocide can be an oxidizing biocide such as chlorine, chlorine dioxide or bromine. Alternatively, the biocide can be a non-oxidizing biocide such as glutaraldehydes, quats, tributyltetradecylphosphonium chloride (TTPC) or tetrakish (hydroxymethyl) phosphonium sulfate (THPS).

In certain illustrative embodiments, the well treatment composition can be utilized for surface treatment jobs or other industrial applications. For example, the sorbent material can be designed to be large enough for a screen filter, so that a stream of water can be passed over the sorbent material with the screen filter near the flow outlet. In certain illustrative embodiments, the well treatment composition can be utilized together with an ion exchange resin bed. The ion exchange resin bed can be utilized to load the sorbent material with biocide. The ion exchange resin bed can also be skid or trailer mounted for mobile applications. Skid mounting would be advantageous because the skid can be swapped out or exchanged without the operators being exposed to the biocide material.

While the disclosed subject matter has been described in detail in connection with a number of embodiments, it is not limited to such disclosed embodiments. Rather, the disclosed subject matter can be modified to incorporate any number of variations, alterations, substitutions or equivalent arrangements not heretofore described, but which are commensurate with the scope of the disclosed subject matter.

Additionally, while various embodiments of the disclosed subject matter have been described, it is to be understood that aspects of the disclosed subject matter may include only some of the described embodiments. Accordingly, the disclosed subject matter is not to be seen as limited by the foregoing description, but is only limited by the scope of the appended claims.

What is claimed is:

1. A well treatment material for introduction into a subterranean formation, the well treatment material comprising a biocide collected onto a sorbent, wherein the biocide is capable of being desorbed at a generally constant rate over an extended period of time into the subterranean formation, and wherein the biocide consists essentially of chlorine dioxide.

2. The well treatment material of claim 1, wherein the sorbent material comprises one or more of an absorbent material and an adsorbent material.

3. The well treatment material of claim 1, wherein the sorbent comprises one or more of silica gel and graphite.

4. The well treatment material of claim 1, wherein the concentration of chlorine dioxide in the well treatment material is up to about 35 percent.

5. An oxidizing material for use in a producing well, the oxidizing material comprising a biocide collected onto a sorbent material, wherein the biocide consists essentially of chlorine dioxide.

6. The oxidizing material of claim 5, wherein the sorbent material comprises one or more of an absorbent material and an adsorbent material.

7. The oxidizing material of claim 5, wherein the sorbent material comprises one or more of silica gel and graphite.

8. The oxidizing material of claim 5, wherein the sorbent material is disposed in a proppant pack.

9. An oxidizing material for use in a hydraulic fracturing operation, the oxidizing material comprising a biocide collected onto a sorbent material, wherein the biocide consists essentially of chlorine dioxide.

10. The oxidizing material of claim 9, wherein the sorbent material comprises one or more of an absorbent material and an adsorbent material.

11. The oxidizing material of claim 9, wherein the sorbent material comprises one or more of silica gel and graphite.

12. The oxidizing material of claim 11, wherein the sorbent material is disposed in a proppant pack.

13. A fracturing fluid comprising: a carrier fluid; a polymer that is soluble in the carrier fluid; a proppant; and an oxidizing material comprising a biocide collected onto a sorbent material, wherein the biocide consists essentially of chlorine dioxide.

14. The fracturing fluid of claim 13, wherein the sorbent material comprises one or more of an absorbent material and an adsorbent material.

15. The fracturing fluid of claim 13, wherein the sorbent material comprises one or more of silica gel and graphite.

\* \* \* \* \*